US011837355B2

United States Patent
Kim

(10) Patent No.: US 11,837,355 B2
(45) Date of Patent: Dec. 5, 2023

(54) SYSTEM AND METHOD FOR ASSISTING VERIFICATION OF LABELING AND CONTOURING OF MULTIPLE REGIONS OF INTEREST

(71) Applicant: INFINITT HEALTHCARE CO., LTD., Seoul (KR)

(72) Inventor: Han Young Kim, Seoul (KR)

(73) Assignee: INFINITT HEALTHCARE CO., LTD., Seoul (KR)

( * ) Notice: Subject to any disclaimer, the term of this patent is extended or adjusted under 35 U.S.C. 154(b) by 305 days.

(21) Appl. No.: 17/153,179

(22) Filed: Jan. 20, 2021

(65) Prior Publication Data

US 2022/0199231 A1    Jun. 23, 2022

(30) Foreign Application Priority Data

Dec. 22, 2020  (KR) .......................... 10-2020-0180446

(51) Int. Cl.
*G16H 30/40* (2018.01)
*G06T 7/00* (2017.01)
*G16H 30/20* (2018.01)
*G06V 10/25* (2022.01)

(52) U.S. Cl.
CPC ........... *G16H 30/40* (2018.01); *G06T 7/0012* (2013.01); *G06V 10/25* (2022.01); *G16H 30/20* (2018.01)

(58) Field of Classification Search
CPC ........ G16H 30/40; G16H 30/20; G06V 10/25; G06T 7/0012
See application file for complete search history.

(56) References Cited

U.S. PATENT DOCUMENTS

| | | | |
|---|---|---|---|
| 8,983,189 B2 * | 3/2015 | Dror ......................... | G06T 7/12 |
| | | | 382/173 |
| 9,304,982 B2 * | 4/2016 | Grady ..................... | G06T 17/00 |
| 9,697,611 B2 * | 7/2017 | Chang ...................... | G06T 7/11 |
| 10,032,272 B2 * | 7/2018 | Jo ........................... | G06T 7/149 |
| 10,839,514 B2 | 11/2020 | Accomazzi et al. | |

(Continued)

FOREIGN PATENT DOCUMENTS

JP      2020-533075 A      11/2020
KR      10-1287382 B1      7/2013

(Continued)

*Primary Examiner* — John Villecco
*Assistant Examiner* — Courtney Joan Nelson
(74) *Attorney, Agent, or Firm* — United One Law Group LLC; Kongsik Kim; Jhongwoo Peck

(57) ABSTRACT

Disclosed herein are a system and method for assisting the verification of the contouring of medical images. A system for assisting the verification of the contouring of medical images according to an embodiment of the present invention receives a medical image set including a plurality of medical images via the communication interface, receives the result information of contouring performed on a plurality of regions of interest (ROIs) on the plurality of medical images in the medical image set via the communication interface, calculates the feature value of each of the plurality of ROIs, corresponding to the result information of the contouring, for each of the plurality of medical images, and displays the boundary of each of the plurality of ROIs corresponding to the result information of the contouring by projecting the boundary onto a reference plane.

14 Claims, 7 Drawing Sheets

(56) References Cited

U.S. PATENT DOCUMENTS

| | | | | |
|---|---|---|---|---|
| 2009/0067700 | A1* | 3/2009 | Maton | A61B 6/5229 |
| | | | | 382/173 |
| 2015/0297916 | A1* | 10/2015 | Chen | G06T 7/13 |
| | | | | 600/1 |
| 2017/0084041 | A1* | 3/2017 | Albrecht | G06T 7/50 |
| 2019/0239926 | A1* | 8/2019 | Pavlovskaia | G06V 10/46 |
| 2020/0176112 | A1 | 6/2020 | Sati et al. | |
| 2020/0320709 | A1 | 10/2020 | Geipel et al. | |

FOREIGN PATENT DOCUMENTS

| | | |
|---|---|---|
| KR | 10-1404345 B1 | 6/2014 |
| KR | 10-2017-0143293 A | 12/2017 |
| KR | 10-1919908 B1 | 11/2018 |

* cited by examiner

SYSTEM AND METHOD FOR ASSISTING VERIFICATION OF LABELING AND CONTOURING OF MULTIPLE REGIONS OF INTEREST

CROSS-REFERENCE TO RELATED APPLICATION

This application claims the benefit of Korean Patent Application No. 10-2020-0180446 filed on Dec. 22, 2020, which is hereby incorporated by reference herein in its entirety.

BACKGROUND

1. Technical Field

The present invention relates to technology regarding medical image processing, and more particularly to technology for verifying the integrity of the labeling and/or contouring of successive medical images.

2. Description of the Related Art

In a diagnosis assistance system using medical images, training data, which is a basis for decisions, is significantly important. In order to generate training data for training an artificial neural network, the regions of interest (ROIs) of medical images are segmented, the results of the segmentation are marked as contours, and identifiable labels are allocated to the contours (or images including contours).

For example, in Korean Patent No. 10-1919908 entitled "Method for Assisting Labeling of Medical Images and Apparatus using the Same," there is disclosed a labeling process for generating labels for a plurality of medical images. In Korean Patent No. 10-1919908, both the process of labeling medical images and the process of automatically assisting labeling are disclosed.

In the case of computed tomography (CT) or magnetic resonance (MR) images, the contouring of an overall medical image set acquired through one imaging is used not only for labeling for the generation of training data but also for image-guided radiation therapy (IGRT).

In general, contouring is the process of extracting the contour of an object of interest from an image, and is widely used in the field of image processing because an object can be represented concisely and easily to analyze. In the field of medical image processing, contouring can be used for diagnosis, treatment, and prognosis after treatment by using diagnostic images such as computed tomography (CT) images or magnetic resonance (MR) images acquired from patients.

Contouring has considerable significance in image-guided radiation therapy (IGRT). IGRT is a method of irradiating only a tumor area while protecting normal tissue around the tumor as much as possible by planning the location and extent of irradiation using diagnostic images before radiation treatment. For this purpose, it is necessary to input the contour information of normal organs and distinguish between a tumor region and the normal organs.

This contouring process is manually performed by a medical professional in the medical field. Due to the recent development of diagnostic imaging apparatuses, the amount of data in medical images is enormous, and thus the manual contouring performed by a medical professional requires a lot of time, with the result that automatic and semi-automatic contouring is performed. However, a problem arises in that there occurs a difference between the actual boundary of a human organ to be contoured and a contour required by a user.

In Korean Patent No. 10-1404345 entitled "Object Automatic Contouring System for Diagnostic Image and Contouring Method Therefor," there is disclosed an example of the process of contouring an overall medical image set. Despite these efforts, medical professionals manually perform contouring on all medical image sets in the medical field.

Although the technologies disclosed in the prior art documents include attempts to partially replace a contouring or labeling process for all medical images in a medical image set performed in the medical field, only contouring or labeling results that have been manually verified by medical professionals are accepted as valid data in the medical field.

Therefore, there is a demand for a means for assisting the verification of the integrity of the results of contouring or labeling performed manually on all medical images in a medical image set.

SUMMARY

Although the above-described prior art documents, i.e., Korean Patent No. 10-1919908 entitled "Method for Assisting Labeling of Medical Images and Apparatus using the Same" and Korean Patent No. 10-1404345 entitled "Object Automatic Contouring System for Diagnostic Image and Contouring Method Therefor," include attempts to partially replace a contouring or labeling process for all medical images in a medical image set performed in the medical field, only contouring or labeling results that have been manually verified by medical professionals are accepted as valid data in the medical field.

In particular, in order to generate training data for image-guided radiation therapy (IGRT) or the training of an artificial neural network, it is necessary to contour and label all of a plurality of organs included in medical images. Each of the plurality of organs should be treated as an independent region of interest (ROI).

It takes a long time to perform contouring and labeling on a plurality of ROIs for all medical images in a medical image set. Due to the recent development of medical imaging technology, the contouring and labeling of vast amounts of data are required, so that a means of verifying integrity is required.

Furthermore, the results of contouring and labeling vary depending on the skill level of an individual operator, and the possibility that an error occurs also varies depending on the skill level of an individual operator.

Accordingly, an object of the present invention is to provide a means for assisting the verification of the integrity of the results of contouring or labeling performed manually on all medical images in a medical image set.

An object of the present invention is to provide a user interface that enables a user to view a brief analysis result for a vast quantity of labeling and contouring results and the progress of the labeling and contouring results at one time.

An object of the present invention is to provide a user interface that displays various errors found in the process of analyzing labeling and contouring results so that a user can easily find them.

An object of the present invention is to provide a user interface that can easily or automatically correct various errors found in the process of analyzing labeling and contouring results.

According to an aspect of the present invention, there is provided a system for assisting the verification of the contouring of medical images, the system including at least one processor, a user interface, and a communication interface. The at least one processor is further configured to receive a medical image set including a plurality of medical images via the communication interface, to receive the result information of contouring performed on a plurality of regions of interest (ROIs) on the plurality of medical images in the medical image set via the communication interface, to calculate the feature value of each of the plurality of ROIs, corresponding to the result information of the contouring, for each of the plurality of medical images, and to display the boundary of each of the plurality of ROIs corresponding to the result information of the contouring by projecting the boundary onto a reference plane.

The at least one processor may be further configured to detect an error included in the result information of the contouring performed on each of the plurality of ROIs by analyzing the boundary of each of the plurality of ROIs corresponding to the result information of the contouring.

The at least one processor may be further configured to display the detected error based on a visual element that is distinguished from those of a rest area on the reference plane and ROIs where no error is found on the reference plane so that the detected error can be distinguished.

The at least one processor may be further configured to display an error representation image connected to the detected error when it receives a user selection for the detected error via the user interface.

The at least one processor may be further configured to display an ROI representation image corresponding to any selected one of the plurality of ROIs corresponding to the result information of the contouring when it receives a user selection for the any selected region of interest (ROI) via the user interface.

The at least one processor may be further configured to detect an error when the contouring result for at least one of the plurality of ROIs is missing, overlaps or branches unintentionally for at least one first medical image of the plurality of medical images, forms an open curve, forms a sharp point, or forms a fragment not connected to other contouring results.

The at least one processor may be further configured to, when the contouring result is missing, compensate for the missing contouring result by performing automatic interpolation on the at least one first medical image for which the contouring result is missing.

The at least one processor may be further configured to, when the contouring result forms a sharp point, correct the sharp point into a smooth curve using image information around the sharp point.

The at least one processor may be further configured to, when the contouring result forms an open curve or a fragment, correct the error by removing at least one of the open curve and the fragment.

The feature value of each of the plurality of ROIs corresponding to the result information of the contouring may include at least one of the location, number of, volume, and curvature of each of the plurality of ROIs.

The reference plane may be at least one of axial, sagittal and coronal images and a scout image corresponding to a coronal plane that can represent a part of the human body, represented by the overall medical image set, from one side.

The at least one processor may be further configured to provide a dashboard-type user interface that enables a user to view progress of the contouring for the medical image set at one time.

The dashboard type user interface may be configured to display contouring results on the reference plane so that the user can view the progress of the contouring for the overall medical image set at one time, to display a contouring result in association with each user so that the user can view the progress of the contouring for himself or herself, or to display a contouring result in association with each of a plurality of ROIs so that the user can view the progress of the contouring for each of the plurality of ROIs at one time.

According to another aspect of the present invention, there is provided a method for assisting the verification of the contouring of medical images, the method including: receiving, by at least one processor, a medical image set including a plurality of medical images via a communication interface; receiving, by the at least one processor, the result information of contouring performed on a plurality of regions of interest (ROIs) on the plurality of medical images in the medical image set via the communication interface; calculating, by the at least one processor, the feature value of each of the plurality of ROIs, corresponding to the result information of the contouring, for each of the plurality of medical images; and displaying, by the at least one processor, the boundary of each of the plurality of ROIs corresponding to the result information of the contouring by projecting the boundary onto a reference plane.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
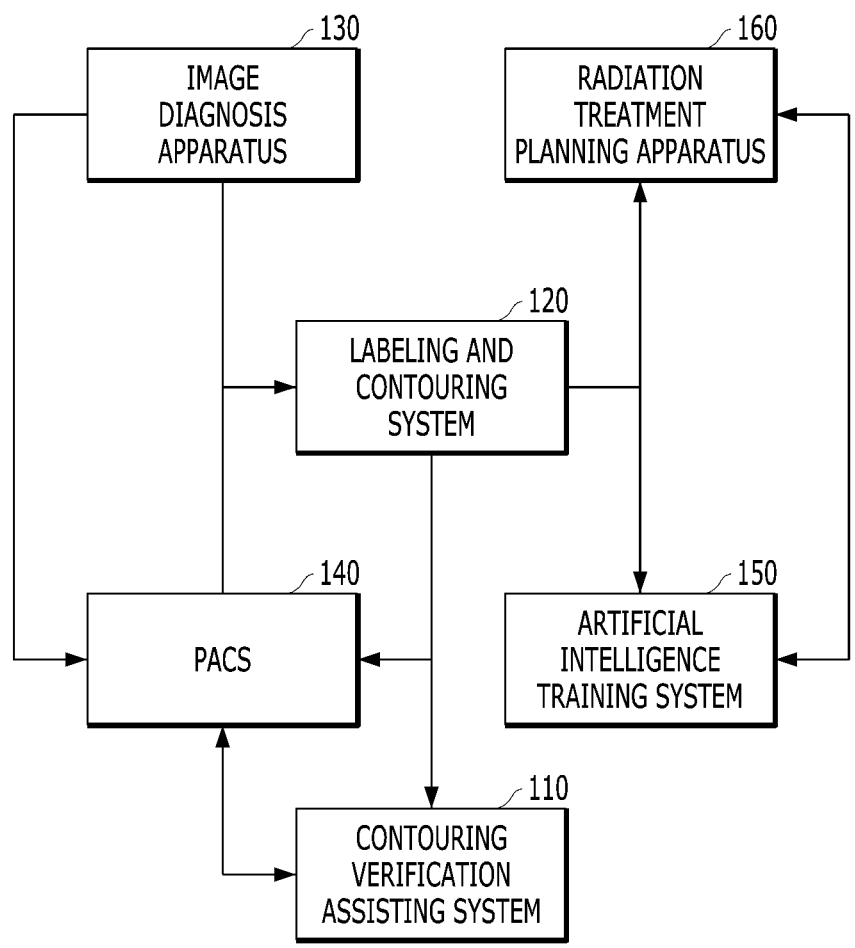
FIG. 1 is a diagram showing relationships between a system for assisting the verification of the contouring of medical images according to an embodiment of the present invention and peripheral systems.

Other objects and features of the present invention in addition to the above-described objects will be apparent from the following description of embodiments taken with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Among the components of the present invention, the components known to those skilled in the art prior to the filing of the present application will be described as parts of the configuration of the present invention in this specification as necessary, but the descriptions thereof may be omitted when it is considered that the descriptions of the items obvious to those skilled in the art may make the spirit of the invention obscure. In addition, for the items omitted in the present specification, the descriptions thereof may be replaced by notifying that they are known to those skilled in the art through prior art documents, such as Korean Patent No. 10-1919908 entitled "Method for Assisting Labeling of Medical Images and Apparatus using the Same" and Korean Patent No. 10-1404345 entitled "Object Automatic Contouring System for Diagnostic Image and Contouring Method Therefor," cited therein.

Furthermore, a description of a configuration for alignment based on the positions of individual medical image slices in a configuration for projecting the results of the contouring of regions of interest onto a reference plane image (an axial, sagittal, coronal, and/or coronal scout image) or displaying the results of the contouring of regions of interest in comparison with the reference plane image according to the present invention may be replaced by the corresponding description of Korean Patent No. 10-1287382 entitled "Medical Image Processing and Display Apparatus and Method Using Attribute Information and Image Characteristic Information."

Some of the items disclosed by these prior art documents are related to the problem to be solved by the present invention, and some of the solutions adopted by the present invention may be borrowed from also applied to these prior art documents.

In the following description given in conjunction with FIGS. 1 to 5, descriptions of the items considered to be well-known technologies in the art to which the present invention pertains may be omitted as necessary or may be replaced by citing prior art documents in order to prevent the gist of the present invention from being obscured.

Furthermore, some or all of the components of the prior art documents cited above and the prior art documents to be cited later are related to the problem to be solved by the present invention, and some of the solutions adopted by the present invention may be borrowed from the prior art documents.

Among the components disclosed in the prior art documents, only the items also included in order to specify the present invention will be considered to be parts of the configuration of the present invention. In this case, among the components disclosed in the prior art documents, only the components not contrary to the object of the present invention may be considered to be parts of the configuration of the present invention.

Details of the present invention will be described below through the embodiments of FIGS. 1 to 5.

FIG. 1 is a diagram showing relationships between a system 110 for assisting the verification of the contouring of medical images according to an embodiment of the present invention and peripheral systems.

A labeling and contouring system 120 and/or the contouring verification assisting system 110 may receive a medical image set, including a plurality of medical images, from an image diagnosis apparatus 130 or a picture archiving and communication system (PACS) 140. The image diagnosis apparatus 130 refers to a modality capable of acquiring a medical image of an anatomical structure inside a human body, such as an ultrasound imaging scanner, a computed tomography (CT) scanner, or a magnetic resonance imaging (MRI) scanner.

The medical image set acquired by the image diagnosis apparatus 130 may be directly transferred from the image diagnosis apparatus 130 to the labeling and contouring system 120 and/or the contouring verification assisting system 110, or may be stored in the PACS 140 and then transferred from the PACS 140 to the labeling and contouring system 120 and/or the contouring verification assisting system 110.

The contouring results derived by the labeling and contouring system 120 may be transferred to an artificial intelligence training system 150 and/or a radiation treatment planning apparatus 160 as contour information for the medical image set through the approval of a user.

The contouring results derived by the labeling and contouring system 120 may be labeled through the approval of a user, and labeling information may be used as training data used to assist the training of an artificial neural network on medical images in the artificial intelligence training system 150. The artificial intelligence training system 150 may train various kinds of artificial intelligence (AI), such as an artificial neural network (ANN), a rule-based AI, a mixed/hybrid version of rule-based AI and ANN, and so on.

The contouring results derived by the labeling and contouring system 120 may be transferred to the radiation treatment planning apparatus 160 and used to establish a treatment plan for IGRT through the approval of a user.

The contouring verification assisting system 110 may include at least one processor, memory, storage, a user interface, and/or a communication interface therein. The contouring verification assisting system 110 corresponds to, e.g., a computing system (not shown), and the computing system may include at least one processor, memory, storage, a database, a user interface, and/or a communication interface. The following operations and functions may be performed by the processor in the computing system, and the processor may perform the following operations and functions in cooperation with at least one of the memory, the storage, the database, the user interface, and/or the communication interface.

The contouring verification assisting system 110 may receive contouring result information generated by the labeling and contouring system 120 and performed on a plurality of regions of interest on the plurality of medical images in the medical image set. In this case, the contouring result information may be directly transferred from the labeling and contouring system 120 to the contouring verification assisting system 110, or may be stored in the PACS 140 and then transferred from the PACS 140 to the contouring verification assisting system 110.

The main components and functions of the present invention may be provided to medical sites in the form of computer-readable program instructions, and the medical image contouring service and/or method according to the present invention may be provided to a user in such a manner that the program instructions are stored or loaded and then executed by the at least one processor and/or the memory.

Detailed descriptions of the configuration in which the main components and functions of the present invention are performed by a computing system including a processor, memory, storage, a database, a user interface, and/or a communication interface and implemented by program instructions may be applied for the implementation of the present invention by being borrowed by a person skilled in the art within the scope suitable for the purpose of the present invention from the foregoing prior art documents, e.g., Korean Patent No. 10-1919908 entitled "Method for Assisting Labeling of Medical Images and Apparatus using the Same," Korean Patent No. 10-1404345 entitled "Object Automatic Contouring System for Diagnostic Image and Contouring Method Therefor," and Korean Patent No. 10-1287382 entitled "Medical Image Processing and Display Apparatus and Method Using Attribute Information and Image Characteristic Information." Since it is determined that more detailed descriptions thereof may make the gist of the present invention obscure, they are replaced by citing these foregoing prior art documents.

Figure 2:
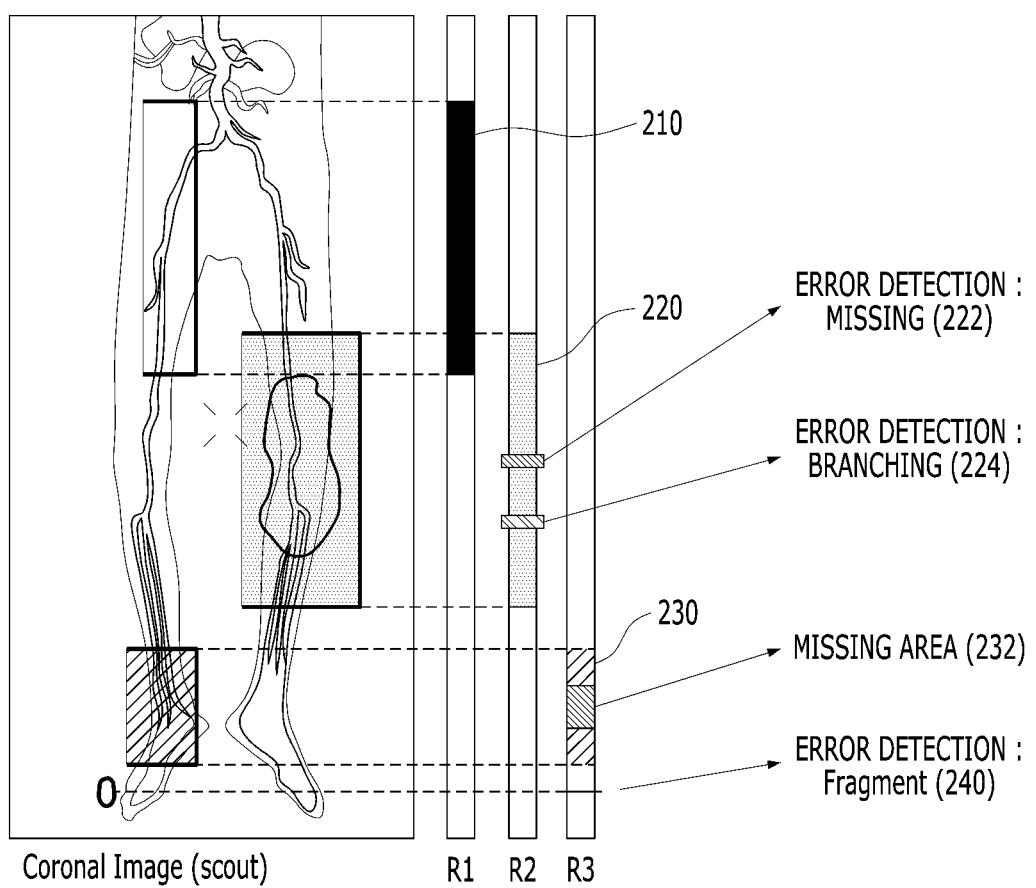
FIG. 2 is a view showing a user interface menu provided by the system for assisting the verification of the contouring of medical images according to the embodiment of the present invention.

FIG. 2 is a view showing a user interface menu provided by the system 110 for assisting the verification of the contouring of medical images according to the embodiment of the present invention.

In FIG. 2, a scout image photographed based on a coronal plane is shown as a reference plane image. A first ROI R1, a second ROI R2, and a third ROI R3 are visualized and displayed on the reference plane image.

The first ROI R1 is an ROI including blood vessels in the thigh, and information into which the boundary and volume of the first ROI R1 are incorporated is marked in the first index area 210 of a bar graph corresponding to the first ROI R1 in accordance with the location coordinate thereof in the z-axis direction on the scout image.

The second ROI R2 is an ROI including blood vessels around the knee, and information into which the boundary and volume of the second ROI R2 are incorporated is marked in the second index area 220 of a bar graph corresponding to the second ROI R2 in accordance with the location coordinate thereof in the z-axis direction on the scout image.

In this case, the contouring verification assisting system 110 may detect an error area 222 in which R2 contour information is missing from a specific slice image based on the boundary and volume information of the second ROI R2 projected onto the second index area 220.

Meanwhile, the contouring verification assisting system 110 may detect an error area 224 in which the R2 contour information branches unintentionally from a specific slice image based on the boundary and volume information of the second ROI R2 projected onto the second index region 220.

The third ROI R3 is an ROI including tissue around the ankle, and information into which the boundary and volume of the third ROI R3 are incorporated is marked in the third index area 230 of a bar graph corresponding to the third ROI R3 in accordance with the location coordinate thereof in the z-axis direction on the scout image.

In this case, the contouring verification assisting system 110 may detect an error area 232 in which the R3 contour information is missing from a specific slice image based on the boundary and volume information of the third ROI R3 projected onto the third index region 230.

In FIG. 2, among the contour results, a fragment/piece that is not connected to other contour results may be detected. The fragment/piece of FIG. 2 is contouring information that is anatomically or clinically insignificant because it is not connected to other contour results and/or other pieces of ROI information. In this case, the contouring verification assisting system 110 may detect an error area 240 corresponding to the fragment/piece.

The error areas 222, 224, 232, and 240 detected in FIG. 2 are all distinguished from other areas within the reference plan image (the coronal scout image in FIG. 2), and are also marked using a visual element that is visually distinguished from that of the index areas 210, 220, and 230 of other ROIs in which no errors are found. In this case, the visual element may refer to a color, a pattern, and/or the shape of a mark.

According to an embodiment of the present invention, the contouring verification assisting system 110 may display and visualize the index areas 210, 220, and 230 so that a user can view the ROI information displayed on the reference plane image at one time. In this case, the contouring verification assisting system 110 may not detect an error before a request from the user, and may provide a user interface menu that visualizes the index areas 210, 220, and 230 and the fragment/piece error area 240 so that the user can recognize them.

For example, in the second index area 220, a slice corresponding to the missing error area 222 will be displayed with contour information missing, so that a user may recognize a discontinuous portion in the second index area 220 and recognize an error in the corresponding portion by himself or herself.

According to another embodiment of the present invention, the contouring verification assisting system 110 may automatically detect the index areas 210, 220, and 230 and the fragment/piece error area 240 in response to a user's input.

According to another embodiment of the present invention, the contouring verification assisting system 110 may automatically detect the index areas 210, 220, and 230 and the fragment/fragment error area 240 even when the user does not provide a special input.

Figure 3:
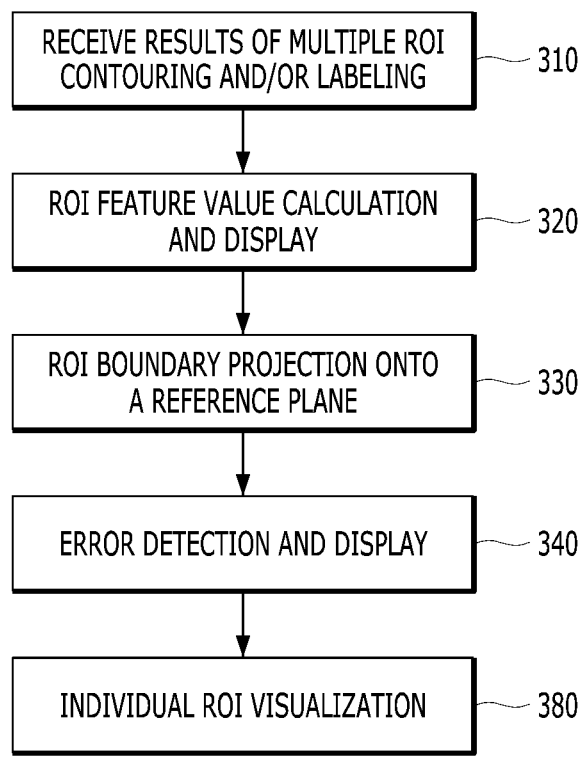
FIG. 3 is a block diagram showing functions provided by the system for assisting the verification of the contouring of medical images according to the embodiment of the present invention.

FIG. 3 is a block diagram showing functions provided by the system 110 for assisting the verification of the contouring of medical images according to the embodiment of the present invention.

In block 310, the contouring verification assisting system 110 receives the result information of contouring, performed on a plurality of ROIs on a plurality of medical images in a medical image set, from the PACS 140 and/or the labeling and contouring system 120 via an internal communication interface.

In block 320, at least one processor inside the contouring verification assisting system 110 calculates the feature value of each of the plurality of ROIs corresponding to the contouring result information for each of the plurality of medical images. Furthermore, in block 330, the at least one processor inside the contouring verification assisting system 110 projects and displays the boundary of each of the plurality of ROIs corresponding to the contouring result information onto a reference plane.

In block 340, the at least one processor inside the contouring verification assisting system 110 may detect an error included in the result information of the contouring performed on each of the plurality of ROIs by analyzing the boundary of each of the plurality of ROIs corresponding to the contouring result information.

In block 340, the at least one processor inside the contouring verification assisting system 110 may display the detected error based on a visual element that is distinguished from those of the rest area on the reference plane and the ROIs in which no error is found on the reference plane so that the detected errors can be distinguished. In this case, the detected error may be visualized to be distinguished using a color, a pattern, or the shape of a mark that is distinguished from those of the rest area and the ROIs in which no errors are found.

When the at least one processor inside the contouring verification assisting system 110 receives a user selection for the detected error via the user interface, it may display an error representation image connected to the detected error. In this case, when the user selects the detected error, movement may be made to an area in which the error is present and a corresponding portion may be displayed, or an image connected to the corresponding area may be displayed to represent the corresponding area.

In block 380, when the at least one processor inside the contouring verification assisting system 110 receives a user selection for any one of the plurality of ROIs corresponding to the contouring result information via the user interface, it may visualize the selected individual ROI. In this case, the selected individual ROI may be displayed as an ROI representation image corresponding to the selected individual ROI. When the individual ROI is selected, the selected ROI may be output in a cine format or visualized in a three-dimensional (3D) space. An example in which the selected ROI is visualized in a 3D space is volume rendering representation.

The feature value of each of the plurality of ROIs corresponding to the contouring result information may include at least one of a location, number, volume, and curvature of each of the plurality of ROIs.

The reference plane may be at least one of axial, sagittal and coronal images and a scout image corresponding to a coronal plane that can represent a part of the human body represented by the overall medical image set (an overall range covered by the medical image set in the parts of the human body) from one side. Each of the plurality of medical images displayed on the reference plane may be visualized as bar-shaped index areas in accordance with the coordinates thereof in the z-axis direction, as illustrated in FIG. 2.

The at least one processor inside the contouring verification assisting system 110 may provide a dashboard-type user interface that enables a user to view the progress of contouring for the medical image set at one time.

The dashboard-type user interface may display contouring results on the reference plane so that the user can view the progress of contouring for the overall medical image set at one time, may display a contouring result in association with each user so that the user can view the progress of contouring for himself or herself, or may display a contouring result in association with each of a plurality of ROIs so that the user can view the progress of contouring for each of the plurality of ROIs at one time.

The dashboard-type user interface may be visualized such that the contouring results of multiple users can be compared at the same time and accuracy and integrity can be evaluated for each user.

Figure 4:
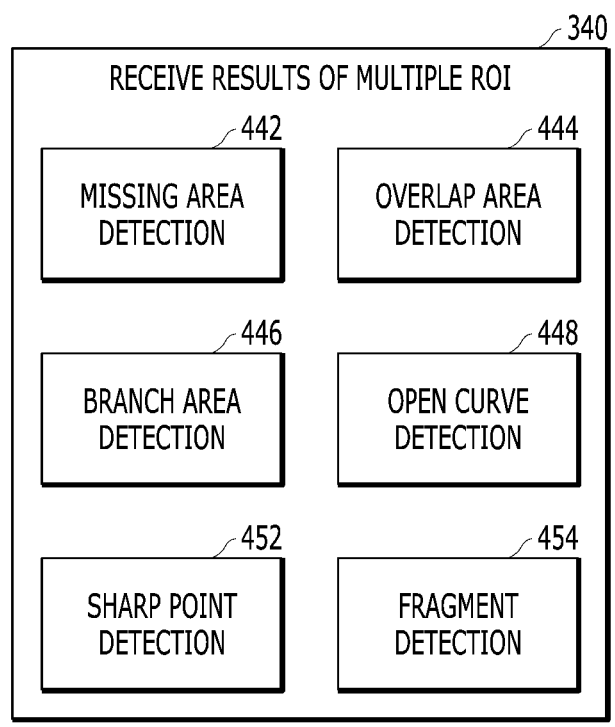
FIG. 4 is a block diagram showing the detailed functions of the error detection and display function of FIG. 3.

FIG. 4 is a block diagram showing the detailed functions of the error detection and display function 340 of FIG. 3.

In block 442, the at least one processor inside the contouring verification assisting system 110 may detect an index area corresponding to at least one first medical image of the plurality of medical images as a missing area when a contouring result for at least one of the plurality of ROIs is missing for the first medical image.

In block 444, the at least one processor inside the contouring verification assisting system 110 may detect an index area corresponding to at least one first medical image of the plurality of medical images as an overlap area when a contouring result for at least one of the plurality of ROIs overlaps for the at least one first medical image.

In block 446, the at least one processor inside the contouring verification assisting system 110 may detect an index area corresponding to at least one first medical image of the plurality of medical images as a branch area when a contouring result for at least one of the plurality of ROIs branches unintentionally for the at least one first medical image.

In block 448, the at least one processor inside the contouring verification assisting system 110 may detect an open curve as an error when a contouring result for at least one of the plurality of ROIs forms the open curve for at least one first medical image of the plurality of medical images. Furthermore, an index area corresponding to the at least one first medical images corresponding to the open curve may be displayed as an index image indicative of an open curve error.

In block 452, the at least one processor inside the contouring verification assisting system 110 may detect a sharp point as an error when a contouring result for at least one of the plurality of ROIs forms the sharp point for at least one first medical image of the plurality of medical images. Furthermore, an index area corresponding to the at least one first medical images corresponding to the sharp point may be displayed as an index image indicative of a sharp point error.

In block 454, the at least one processor inside the contouring verification assisting system 110 may detect a fragment/piece not connected to other contouring results as an error when a contouring result for at least one of the plurality of ROIs forms the fragment/piece for at least one first medical image of the plurality of medical images. Furthermore, an index area corresponding to the at least one first medical images corresponding to the fragment/piece may be displayed as an index image indicative of a fragment/piece error.

Figure 5:
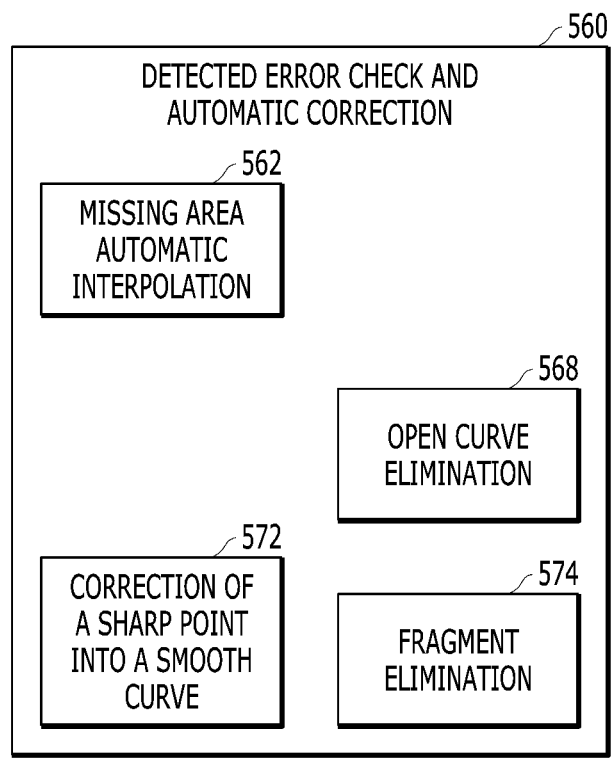
FIG. 5 is a block diagram showing an error check and automatic correction function provided by the system for assisting the verification of the contouring of medical images according to the embodiment of the present invention.

FIG. 5 is a block diagram showing an error check and automatic correction function provided by the system 110 for assisting the verification of the contouring of medical images according to the embodiment of the present invention.

In block 562, at least one processor inside the contouring verification assisting system 110 may compensate for a missing contouring result for at least one first medical image by performing automatic interpolation on the at least one first medical image when the contouring result for the at least one first medical image is missing.

In block 572, the at least one processor inside the contouring verification assisting system 110 may correct a sharp point into a smooth curve using image information around the sharp point when a contouring result forms the sharp point.

In blocks 568 and 574, the at least one processor inside the contouring verification assisting system 110 may correct an error by removing at least one of an open curve and a fragment/piece when a contouring result forms the open curve or the fragment/piece.

Figure 6:
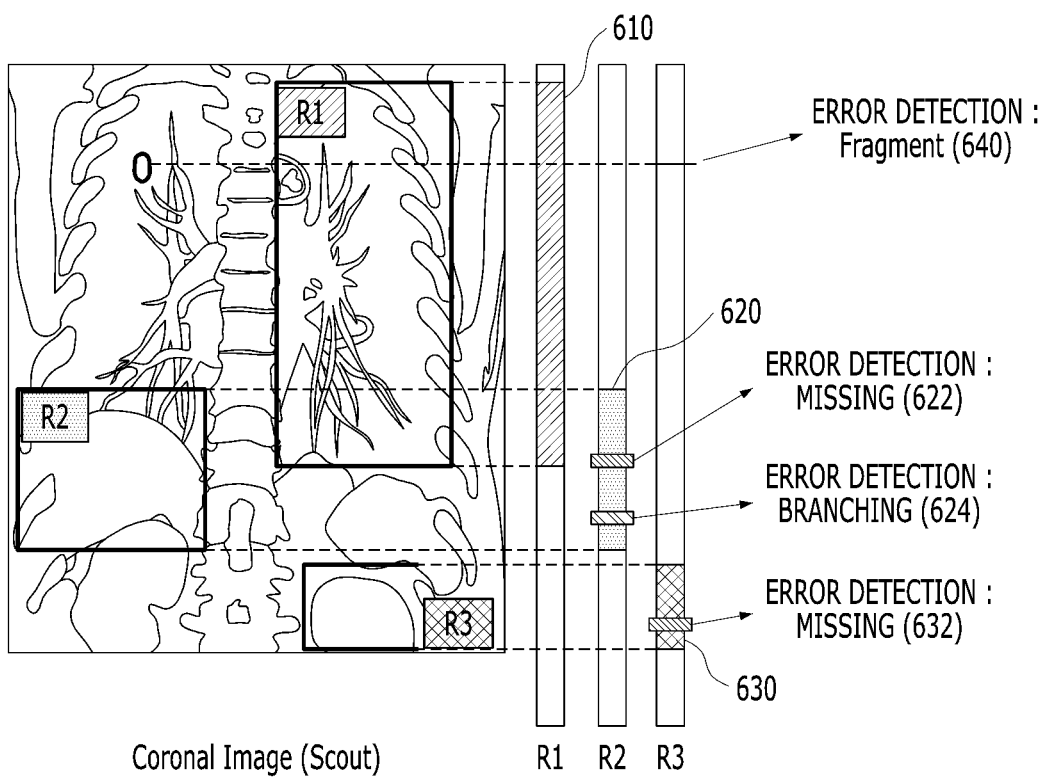
FIG. 6 is a view showing a user interface menu provided by the system for assisting the verification of the contouring of medical images according to the embodiment of the present invention.

FIG. 6 is a view showing a user interface menu provided by the system 110 for assisting the verification of the contouring of medical images according to the embodiment of the present invention.

In FIG. 6, there is shown an embodiment in which ROIs R1, R2, and R3 correspond to respective organs. In addition, in order to clearly reveal that the ROIs R1, R2, and R3 correspond to the organs, respectively, reference characters "R1," "R2," and "R3" indicating the ROIs may be displayed in a more intuitive form.

In FIG. 6, a scout image photographed based on a coronal plane is shown as a reference plane image, as in FIG. 2. The first ROI R1, the second ROI R2, and the third ROI R3 are visualized and displayed on the reference plane image.

The first ROI R1 corresponds to the left lung, and information into which the boundary and volume of the first ROI R1 are incorporated is marked in the first index area 610 of a bar graph corresponding to the first ROI R1 in accordance with the location coordinate thereof in the z-axis direction on the scout image.

The second ROI R2 corresponds to the liver, and information into which the boundary and volume of the second ROI R2 are incorporated is marked in the second index area 620 of a bar graph corresponding to the second ROI R2 in accordance with the location coordinate thereof in the z-axis direction on the scout image.

In this case, the contouring verification assisting system 110 may detect an error area 622 in which R2 contour information is missing from a specific slice image based on the boundary and volume information of the second ROI R2 projected onto the second index area 620.

Meanwhile, the contouring verification assisting system 110 may detect an error area 624 in which the R2 contour information branches unintentionally from a specific slice image based on the boundary and volume information of the second ROI R2 projected onto the second index region 620.

The third ROI R3 is an ROI corresponds to the kidney, and information into which the boundary and volume of the third ROI R3 are incorporated is marked in the third index area 630 of a bar graph corresponding to the third ROI R3 in accordance with the location coordinate thereof in the z-axis direction on the scout image.

In this case, the contouring verification assisting system 110 may detect an error area 632 in which the R3 contour information is missing from a specific slice image based on the boundary and volume information of the third ROI R3 projected onto the third index region 630.

In FIG. 6, among the contour results, a fragment/piece that is not connected to other contour results may be detected. The fragment/piece of FIG. 6 is contouring information that is not anatomically or clinically significant because it is not connected to other contour results and/or other pieces of ROI information. In this case, the contouring verification assisting system 110 may detect an error area 640 corresponding to the fragment/piece.

The error areas 622, 624, 632, and 640 detected in FIG. 6 are all distinguished from other areas within the reference plan image (the coronal scout image in FIG. 2), and are also marked using a visual element that is visually distinguished from that of the index areas 610, 620, and 630 of other ROIs in which no errors are found. In this case, the visual element may refer to a color, a pattern, and/or the shape of a mark.

The embodiment illustrated in FIGS. 2 and 6, each of the plurality of ROIs corresponding to the result information of the contouring may be displayed by projecting the boundary and/or occupied area onto the reference plane. For example, the boundary may mean both of the boundary on the z axis and the occupied area on the x-y plane. The boundary on the z axis of each ROIs may be projected onto index area respectively and may be clearly displayed to the user. The occupied area on the x-y plane of each ROIS may be displayed via a plurality of kinds of representative images such as shown in FIG. 7.

Although the scout image in a coronal plane has been introduced as a reference plane image in FIGS. 2 and 6, at least one of an axial image, a sagittal image, and a coronal image may be used as a reference plane image in another embodiment of the present invention. In addition, in FIGS. 2 and 6, there has been provided the user interface in which the bars on which the index images are marked make it easy to detect errors in which a contouring result is missing or overlaps on a per-slice basis in accordance with the z axis. In contrast, in another embodiment of the present invention, there may be provided a user interface that is visualized for at least one of the x axis and the y axis and makes it easy to detect errors in which a contouring result is missing or overlaps on the x axis, the y axis, or the x-y plane.

Although ROIs have been visualized to be compared with the reference plane image in the embodiments of FIGS. 2 and 6, ROIs may be represented together with 3D volume rendering in another embodiment of the present invention. In this case, the boundary of ROI on the z axis and occupied area of ROI on the x-y plane can be displayed together onto 3D volume at a time. In an embodiment, 3D rendering itself may represent an error regarding the discontinuity of contouring information. However, when contouring result information is displayed via 3D rendering, the computational load to be processed may increase and thus speed may be delayed, so that it may not be preferred in the medical field.

Figure 7:
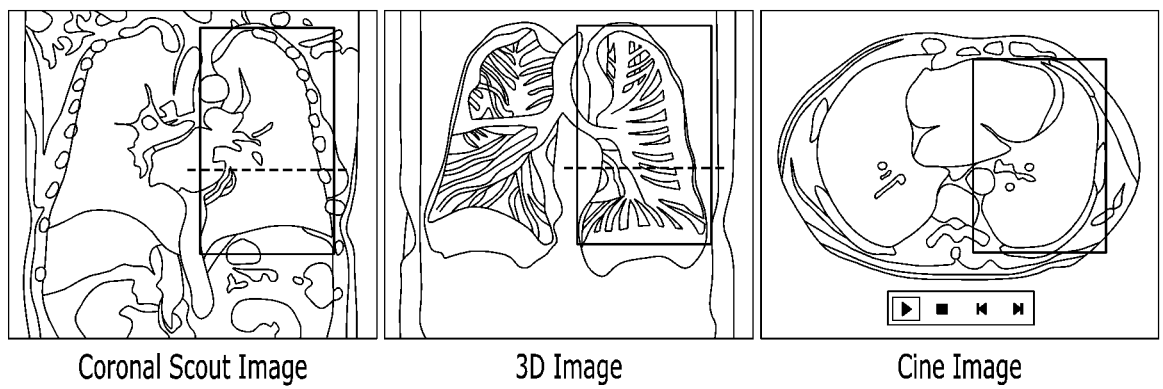
FIG. 7 is a diagram illustrating an example of a detailed image corresponding to an ROI selected by a user in the system for assisting the verification of the contouring of medical images according to the embodiment of the present invention.

FIG. 7 is a diagram illustrating an example of a detailed image corresponding to an ROI selected by a user in the system for assisting the verification of the contouring of medical images according to the embodiment of the present invention.

In the contouring verification assisting system 110, when a user selection command for any one of a plurality of ROIs displayed in response to contouring result information in the reference plane image as shown in FIG. 2 or 6 is received via the user interface, the contouring verification assisting system 110 may visualize the selected individual ROI in block 380. In this case, an example of a representation image in which the selected individual ROI is visualized is shown in FIG. 7.

Referring to FIG. 7, (1) a first representation image in which on the reference plane image, other ROIs are removed and only the selected individual ROI is displayed, (2) a 3D image in which the selected individual ROI is revealed, and (3) a cine image on a slice in the axial plane to which the selected individual ROI is related are shown as examples.

Meanwhile, in the case where an excessively abrupt difference is present between the contouring results of adjacent slices when an anatomical property is taken into consideration, it may also be detected as an error. In this case, a physical property or a biological property may be taken into consideration as the anatomical property. For example, in the case where a contouring result in which an organ indicated by corresponding ROI information changes excessively abruptly between adjacent slices is derived when elasticity is taken into consideration, the contouring verification assisting system 110 may detect and visualize a contouring result, exceeding these constraints, as an error.

Meanwhile, the anatomical property that may be a physical property, a mechanical property, or biological property may be affected by at least one of a user, the type of ROI information (the type of organ), the gender of a patient, and the age of the patient.

In other words, the degree to which an organ can be deformed may vary depending on the age of each patient, and the proportions of body composition may vary depending on the gender of each patient, so that these may also affect the degree to which the organ can be deformed.

Furthermore, anatomical information acting as a contouring constraint may be affected by the disease history of a patient and the treatment/dosing history of the patient. For example, after radiation therapy for liver disease has been received, the liver may harden and anatomical information may be affected.

For example, although a difference in contour between adjacent slices is naturally recognized as an error based on the naked eye and medical expertise of a medical professional by comparing the brightness values of computed tomography (CT) images, there may be cases where the above error cannot be detected by the operation of the machine. The present invention may analyze whether an abrupt change between adjacent contours violates a contouring constraint and detect an error while taking into consideration the above case as well. Since this difference may also be caused by a difference between the skill levels of medical professionals, the contouring verification assisting system 110 according to the present invention may also contribute to improving the skill level of a medical professional.

In this case, a means for detecting an abrupt change in contour between adjacent slices may be implemented, e.g., by calculating the auto-correlation between the contours of the adjacent slices. The contouring constraints may affect the determination of a threshold value that will be compared with the result of the auto-correlation calculation.

Meanwhile, the contouring verification assistance described in the above embodiments may also be used as labeling verification assistance when a labeling result based on a contouring result is accompanied.

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, there may be assisted the verification of the integrity of the results of contouring or labeling performed manually on all medical images in a medical image set.

According to the present invention, there may be provided the user interface that enables a user to view a brief analysis result for a vast quantity of labeling and contouring results and the progress of labeling and contouring results at one time.

According to the present invention, there may be provided the user interface that displays various errors found in the process of analyzing labeling and contouring results so that a user can easily find them.

According to the present invention, there may be provided the user interface that can easily or automatically correct various errors found in the process of analyzing labeling and contouring results.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A system for assisting verification of contouring of medical images, the system comprising:
   at least one processor;
   a user interface; and
   a communication interface,
   wherein the at least one processor is further configured to:
      receive a medical image set including a plurality of medical images via the communication interface;
      receive result information of contouring performed on a plurality of regions of interest (ROIs) on the plurality of medical images in the medical image set via the communication interface;
      display a boundary of each of the plurality of ROIs corresponding to the result information of the contouring by projecting the boundary onto a reference plane showing summarized information regarding the result information of the contouring for the plurality of the medical images;
      detect an error included in the result information of the contouring performed on each of the plurality of ROIs by analyzing the boundary of each of the plurality of ROIs corresponding to the result information of the contouring;
      identify at least one first image corresponding to the detected error from among the plurality of medical images; and
      display the detected error indicating the at least one first image corresponding thereto based on a location of the at least one first image on the reference plane, the location of the at least one first image indicating a relative position in the medical image set.

2. The system of claim 1, wherein the at least one processor is further configured to:
   display the detected error based on a visual element that is distinguished from those of a rest area on the reference plane and ROIs where no error is found on the reference plane so that the detected error can be distinguished.

3. The system of claim 2, wherein the at least one processor is further configured to display an error representation image connected to the detected error when it receives a user selection for the detected error via the user interface.

4. The system of claim 2, wherein the at least one processor is further configured to detect an error when a contouring result for at least one of the plurality of ROIs is missing, overlaps or branches unintentionally for at least one first medical image of the plurality of medical images, forms an open curve, forms a sharp point, or forms a fragment not connected to other contouring results.

5. The system of claim 4, wherein the at least one processor is further configured to:
when the contouring result is missing, compensate for the missing contouring result by performing automatic interpolation on the at least one first medical image for which the contouring result is missing;
when the contouring result forms a sharp point, modify the sharp point into a smooth curve using image information around the sharp point; and
when the contouring result forms an open curve or a fragment, correct the error by removing at least one of the open curve and the fragment.

6. The system of claim 1, wherein the at least one processor is further configured to display an ROI representation image corresponding to any selected one of the plurality of ROIs corresponding to the result information of the contouring when it receives a user selection for the any selected region of interest (ROI) via the user interface.

7. The system of claim 1, wherein the feature value of each of the plurality of ROIs corresponding to the result information of the contouring comprises at least one of a location, number of, volume, and curvature of each of the plurality of ROIs.

8. The system of claim 1, wherein the reference plane is at least one of axial, sagittal and coronal images and a scout image corresponding to a coronal plane that can represent a part of a human body, represented by the overall medical image set, from one side.

9. A system for assisting verification of contouring of medical images, the system comprising:
at least one processor;
a user interface; and
a communication interface,
wherein the at least one processor is further configured to:
receive a medical image set including a plurality of medical images via the communication interface;
receive result information of contouring performed on a plurality of regions of interest (ROIs) on the plurality of medical images in the medical image set via the communication interface;
calculate a feature value of each of the plurality of ROIs, corresponding to the result information of the contouring, for each of the plurality of medical images; and
display a boundary of each of the plurality of ROIs corresponding to the result information of the contouring by projecting the boundary onto a reference plane,
wherein the at least one processor is further configured to provide a dashboard-type user interface that enables a user to view progress of the contouring for the medical image set at one time, and
wherein the dashboard type user interface is configured to:
display contouring results on the reference plane so that the user can view progress of the contouring for the overall medical image set at one time;
display a contouring result in association with each user so that the user can view progress of the contouring for himself or herself; or
display a contouring result in association with each of a plurality of ROIs so that the user can view progress of the contouring for each of the plurality of ROIs at one time.

10. A method for assisting verification of contouring of medical images, the method comprising:
receiving, by at least one processor, a medical image set including a plurality of medical images via a communication interface;
receiving, by the at least one processor, result information of contouring performed on a plurality of regions of interest (ROIs) on the plurality of medical images in the medical image set via the communication interface;
displaying, by the at least one processor, a boundary of each of the plurality of ROIs corresponding to the result information of the contouring by projecting the boundary onto a reference plane showing summarized information regarding the result information of the contouring for the plurality of the medical images;
detecting, by the at least one processor, an error included in the result information of the contouring performed on each of the plurality of ROIs by analyzing the boundary of each of the plurality of ROIs corresponding to the result information of the contouring;
identifying, by the at least one processor, at least one first image corresponding to the detected error from among the plurality of medical images; and
displaying, by the at least one processor, the detected error indicating the at least one first image corresponding thereto based on a location of the at least one first image on the reference plane, the location of the at least one first image indicating a relative position of the detected error in the medical image set.

11. The method of claim 10, further comprising:
displaying, by the at least one processor, the detected error based on a visual element that is distinguished from those of a rest area on the reference plane and ROIs where no error is found on the reference plane so that the detected error can be distinguished.

12. The method of claim 11, further comprising displaying, by the at least one processor, an error representation image connected to the detected error when the at least one processor receives a user selection for the detected error via a user interface.

13. The method of claim 11, further comprising detecting, by the at least one processor, an error when a contouring result for at least one of the plurality of ROIs is missing, overlaps or branches unintentionally for at least one first medical image of the plurality of medical images, forms an open curve, forms a sharp point, or forms a fragment not connected to other contouring results.

14. The method of claim 10, further comprising displaying, by the at least one processor, displaying an ROI representation image corresponding to any selected one of the plurality of ROIs corresponding to the result information of the contouring when the at least one processor receives a user selection for the any selected region of interest (ROI) via a user interface.

* * * * *